United States Patent [19]
Tseng

[11] Patent Number: 6,150,111
[45] Date of Patent: Nov. 21, 2000

[54] METHODS AND KITS FOR RECOMBINING NUCLEIC ACIDS

[75] Inventor: Hung Tseng, Villanova, Pa.

[73] Assignee: The Trustees of the University of Pennsylvania, Philadelphia, Pa.

[21] Appl. No.: 09/270,485

[22] Filed: Mar. 15, 1999

[51] Int. Cl.[7] .............................. C12Q 1/68; C07H 21/04; C12P 19/34; C12N 5/00
[52] U.S. Cl. ......................... 435/6; 435/91.2; 435/91.4; 435/91.42; 435/320.1; 536/23.1; 536/24.31
[58] Field of Search ............................... 435/6, 91.2, 91.4, 435/320.1, 91.42, 810; 536/23.1, 24.31

[56] References Cited

U.S. PATENT DOCUMENTS 5,580,759  12/1996  Yang et al. .......................... 435/91.1

OTHER PUBLICATIONS

Pharmacia, Molecular and Cell Biology Products Catalog 1994, pp. 50–51.
Matsui et al., Production of chimeric protein coded by the fused viral H–ras and human N–ras genes in *Escherichia coli*, Gene, vol. 52m pp. 215–223, 1987.
Cohen et al., 1973, Proc. Natl. Acad. Sci. USA 70(11):3240–3244.
Derbyshire et al., 1988, Science 240:199–201.
Fasbender et al., 1996, J. Biol. Chem. 272:6479–6489.
Hsiao, 1993, Nucleic Acids Research 21:5528–5529.
Kaluz et al., 1992, Nucleic Acids Research 20:4369–4370.
Little, 1981, Lambda Exonuclease: Gene Amplification and Analysis. Eds. J.G. Chirikjian and T.S. Papas, Elsevier, pp. 135–145.
Ma et al., 1989, Gene 58:201–216.
Oldenburg et al., 1997, Nucleic Acids Research 25:451–452.
Raymond et al., 1999, BioTechniques 26:(1):134–141.
Smith et al., 1979, J. Mol. Biol. 51:(2):379–391.
Tseng et al., 1992, Proc. Natl. Acad. Sci. USA 89:10311–10315.
Weiss et al., 1968, J. Biol. Chem. 243(17):4543–4555.

*Primary Examiner*—Robert A. Schwartzman
*Assistant Examiner*—Andrew Wang
*Attorney, Agent, or Firm*—Akin, Gump, Strauss, Hauer & Feld, L.L.P.

[57] ABSTRACT

The invention includes a method for recombining and, optionally, cloning nucleic acids without the use of restriction enzymes or DNA ligase. The method involves recombining an insert and a recipient nucleic acid using custom designed complementary regions to anneal strands from the nucleic acids. The complementary regions on double stranded nucleic acids are exposed by limited digestion of the ends of the nucleic acids. After annealing the digested ends, single stranded gaps on the hybridized nucleic acid are closed to yield a double stranded nucleic acid which may, optionally, be cloned into a microorganism. The invention also includes kits for recombining and, optionally, cloning nucleic acids using the methods of the invention. The invention further includes recombinant nucleic acids prepared using the methods of the invention.

17 Claims, 3 Drawing Sheets

METHODS AND KITS FOR RECOMBINING NUCLEIC ACIDS

STATEMENT REGARDING FEDERALLY SUPPORTED RESEARCH AND DEVELOPMENT

This research was supported in part by U.S. Government funds (National Institute on Aging, Grant number AG14456), and the U.S. Government may therefore have certain rights in the invention.

FIELD OF THE INVENTION

The field of the invention is methods and kits for recombining nucleic acids.

BACKGROUND OF THE INVENTION

Traditional methods for recombining and cloning DNA involve using restriction enzymes and DNA ligase to cut and create cohesive or blunt ends in DNA and then to recombine and link the DNA. Restriction enzymes facilitate the preparation of the desired DNA segments and the process of recombining DNA (Smith et al., 1970, J. Mol. Biol. 51(2):379–391). DNA ligase links two segments of DNA, an insert and a vector such as a plasmid (Weiss et al., 1968, J. Biol. Chem. 243(17):4543–4555). The linked or ligated DNA can be introduced into a microorganism such as E. coli for cloning (Cohen et al., 1973, Proc. Natl. Acad. Sci. USA 70(11):3204–3244). Restriction enzymes aid in recombination by creating cohesive ends on DNA fragments which are used for properly aligning DNA fragments. When the DNA has two different cohesive ends after restriction enzyme treatment, the orientation of the insert in relation to the vector can be controlled.

One common problem with the traditional recombination and cloning method is that nucleic acids do not always have suitable restriction sites. When joining protein coding sequences, restriction sites must flank the sequences of interest and possess cohesive ends compatible with the sites in the vector or another coding sequence into which it is to be inserted. Continuity of the reading frames must be preserved after ligation so that the correct protein results from subsequent DNA transcription and RNA translation processes.

In practice, naturally occurring restriction sites that satisfy such requirements are often not present. A known method of preserving the reading frame is to create new restriction sites using oligonucleotides as linkers or adapters or polymerase chain reaction (PCR), a step which requires one or more rounds of cloning. New restriction sites can be created in PCR by including one or more restriction sites in the PCR primers that are synthesized by chemical means. However, the choice of a new restriction site is often limited because identical sites may be present within the cloning vector or in the sequence to be cloned.

The traditional method is complicated and time consuming, as is evident from a consideration of these problems in the art.

A method was recently described which can be independent of natural restriction sites or in vitro ligation (Ma et al., 1989, Gene 58:201–216; Oldenburg et al., 1997, Nucleic Acids Research 25:451–452). This method is an in vivo method for plasmid construction that takes advantage of the double-stranded break repair pathway in a yeast to achieve precision joining of DNA fragments. However, this method requires synthesis of linkers (60–140 base pairs) from short oligonucleotides and requires assembly by enzymatic methods into the linkers needed (Raymond et al., 1999, BioTechniques 26(1):134–141).

The invention described herein overcomes the problems inherent in the traditional cloning methods and does not require use of restriction endonucleases or DNA ligase.

BRIEF SUMMARY OF THE INVENTION

The invention includes a method of recombining an insert nucleic acid and a recipient nucleic acid. The method comprises the steps of a) digesting the 5' terminus of an end of the insert nucleic acid to yield a 3' overhanging insert portion and a 5' digested insert terminus; b) digesting the 5' terminus of an end of the recipient nucleic acid to yield a 3' overhanging recipient portion and a 5' digested recipient terminus, wherein the 3' overhanging recipient portion and the 3' overhanging insert portion are complementary; and c) annealing the 3' overhanging recipient portion and the 3' overhanging insert portion to yield a double stranded complementary region, whereby the insert nucleic acid and the recipient nucleic acid form a recombined nucleic acid.

In one aspect, the method further includes the step of d) closing single stranded gaps in the recombined nucleic acid.

In another aspect, the method further includes the step of e) introducing the recombined nucleic acid into a microorganism after closing the single stranded gaps.

Preferably, the single stranded gaps are closed using an enzyme selected from the group consisting of a DNA polymerase and a DNA repair enzyme.

In one embodiment the DNA polymerase is T4 DNA polymerase.

More preferably, the enzyme lacks 3'→5' exonuclease activity.

In a preferred embodiment, the 3' overhanging portions have a uniform length of from about 20 to about 30 nucleotide bases.

Preferably, the DNA repair enzyme is the modified (3'→5' exo-) Klenow fragment of E. coli DNA polymerase I.

In one aspect, the complementary region has a length from about 3 to about 10 nucleotide residues.

In a preferred embodiment, the 5' termini are digested using an 5'→3' exonuclease. Preferably, the 5'→3' exonuclease is lambda exonuclease.

Preferably, at least one of the insert nucleic acid and the recipient nucleic acid is prepared by PCR.

In another aspect the insert nucleic acid and the recipient nucleic acid are phosphorylated at their 5' termini.

In a preferred embodiment, the PCR reaction is carried out using a thermophile polymerase and wherein the nucleic acid has blunt ends.

In one embodiment of the method of the invention, the recombined nucleic acid comprises a promoter/regulatory sequence and an in-phase open reading frame.

In a preferred embodiment of the method of the invention, the insert and the recipient nucleic acids are independently selected from the group consisting of a nucleic acid obtained from a human, a nucleic acid encoding a therapeutic agent, and a nucleic acid of a gene vector.

The invention also includes a kit for recombining nucleic acids. The kit comprises a) an exonuclease enzyme; b) a polymerase enzyme, and c) a recombination instructional material.

In one embodiment, the kit further comprises an additional component selected from the group consisting of a sample container, a DNA polymerase, a DNA repair enzyme, an exonuclease buffer, a DNA polymerase buffer, a DNA repair enzyme buffer, and control recipient and insert nucleic acids.

Additionally, the invention includes a nucleic acid made by the method of the invention.

Also included in the invention is a method of recombining an insert nucleic acid and a recipient nucleic acid. The method comprises the steps of a) digesting the 3' terminus of an end of the insert nucleic acid to yield a 5' overhanging insert portion and a 3' digested insert terminus; b) digesting the 3' terminus of an end of the recipient nucleic acid to yield a 5' overhanging recipient portion and a 3' digested recipient terminus, wherein the 5' overhanging recipient portion and the 5' overhanging insert portion are complementary; and c) thereafter annealing the 5' overhanging recipient portion and the 5' overhanging insert portion, whereby the insert nucleic acid and the recipient nucleic acid form a recombined nucleic acid.

In one aspect, the 3' termini are digested using Exonuclease III.

BRIEF DESCRIPTION OF THE DRAWINGS

FIG. 1, comprising FIGS. 1A and 1B, is a pair of diagrams depicting end sequences of the PCR fragment (plasmid vector pRSET-B) used as the recipient nucleic acid and the PCR fragment (basonuclin serine stripe region) used as the insert nucleic acid in the Example described herein. FIG. 1A also lists the DNA sequence (SEQ ID NO: 5) of the vector and the DNA sequence (SEQ ID NO: 6) of the insert on the right end.

FIG. 2, comprising FIGS. 2A, 2B, 2C, and 2D, is a series of illustrations depicting the method for recombining DNA as described in the Example.

FIG. 3, comprising FIGS. 3A, 3B, and 3C, is a trio of images of agarose gels depicting the time course of lambda exonuclease digestion of DNA at 22° C., 10° C. and 0° C., respectively. The digestion time was 0.5 minutes for lane 1, 1 minute for lane 2, 2 minutes for lane 3, 3 minutes for lane 4, 4 minutes for lane 5, 5 minutes for lane 6, 6 minutes for lane 7, 7 minutes for lane 8. Molecular weight markers (M) were included and the approximate sizes of the markers are indicated on the right side of FIG. 3A.

DETAILED DESCRIPTION

The present invention relates to a method of recombining nucleic acids which does not require use of either restriction endonucleases or DNA ligases. This method thus avoids the limitations inherent in prior art recombination methods.

An important advantage of the present invention is that it provides a method for preparing customized cohesive ends of nucleic acids to be recombined. In one embodiment, a combination of PCR primer design and exonuclease digestion are used to prepare nucleic acids for recombination. Because the nucleic acids to be recombined according to this method can be prepared by PCR, one nucleic acid may be rapidly and precisely inserted into almost any desired location of another nucleic acid. This method thus provides much greater flexibility than the traditional method for preparing recombinant nucleic acids.

Another advantage of the method of the invention is that it simplifies recombination or DNA cloning strategies by requiring only selection of appropriate PCR primers. Because DNA ligase is not required in this method, dephosphorylation of nucleic acids to prevent non-desired ligation is not necessary. Also, purification to remove reactants that may result in non-desired ligation products is also unnecessary.

The method of the present invention has a higher recombination efficiency than traditional methods for recombining nucleic acids. Recombination efficiency means the ratio of the number of correct linkages to that of the erroneous linkages. Erroneous linkages are common in the traditional methods due to the self-complementary nature of the cohesive ends created by restriction enzymes. Unlike a restriction enzyme cut, the overhanging portion of the digested nucleic acid in the method of the invention can be designed to avoid symmetry, eliminating self-complementarity. This eliminates non-desired hybridization to portions of the nucleic acids during the recombination procedure, thereby enhancing recombinant frequency.

Furthermore, the method of the present invention is versatile. The method can utilize an available restriction site, if desired. Because the only variable may be selection of appropriate PCR primers, the remaining steps are identical for virtually any kind of nucleic acid fragments, and the method is therefore suitable for automation.

Definitions

The articles "a" and "an" are used herein to refer to one or to more than one (i.e. to at least one) of the grammatical object of the article. By way of example, "an element" means one element or more than one element.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids comprising bases other than the five biologically occurring bases (adenine, guanine, thymine, cytosine, and uracil).

It is not intended that the present invention be limited by the nature of the nucleic acid employed. The target nucleic acid may be a naturally occurring or synthesized nucleic acid. The nucleic acid may be obtained from a viral, bacterial, animal, or plant source. The nucleic acid may be DNA or RNA, and may exist in a double-stranded, single-stranded, or partially double-stranded form. Furthermore, the nucleic acid may be found as part of a virus or other macromolecule, such as a polylysine condensation of DNA in the form of adenovirus (e.g., Fasbender et al., 1996, J. Biol. Chem 272:6479–89).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (e.g., Gait, 1985, Oligonucleotide Synthesis: A Practical Approach, IRL Press, Oxford, England). RNAs may be produced in high yield using in vitro transcription using plasmids such as SP65 (Promega Corporation, Madison, Wis.).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate, phosphorothioate, posphorodithioate, phosphoramidate, methoxyethyl phosphoramidate, formacetal, thioformacetal, diisopropylsilyl, acetamidate, carbamate, dimethylene-sulfide ($—CH_2—S—CH_2$), dimethylene-sulfoxide ($—CH_2—SO—CH_2$), dimethylene-sulfone ($—CH_2—SO_2—CH_2$), 2'—O—alkyl, and 2'-deoxy-2'-fluoro phosphorothioate internucleoside linkages are well known in the art (Uhlmann et al., 1990, Chem. Rev. 90:543–584; Schneider et al., 1990, Tetrahedron Lett. 31:335).

The nucleic acids may be purified by any suitable means, as are well known in the art. For example, the nucleic acids can be purified by reverse phase or ion exchange HPLC, size exclusion chromatography, or gel electrophoresis. Of course, the skilled artisan will recognize that the method of purification will depend in part on the size of the DNA to be purified.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 751%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, an "instructional material" includes a publication, a recording, a diagram, or any other tangible medium of expression which can be used to communicate the method of the invention for recombining and/or cloning nucleic acids. The instructional material of the kit of the invention may, for example, be affixed to a container which contains the enzymes used in the method of the invention or be shipped together with a container which contains the enzymes. Alternatively, the instructional material may be shipped separately from the container with the intention that the instructional material and the enzymes be used cooperatively by the recipient.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, bacteriophage, plasmids, and viruses. Thus, the term "vector" includes, but is not limited to, an autonomously replicating plasmid or a virus. The term should also be construed to include non-plasmid and non-viral compounds which facilitate transfer of nucleic acid into cells, such as, for example, polylysine compounds, liposomes, microprojectiles, and the like. Examples of virus vectors include, but are not limited to, adenoviral vectors, adeno-associated virus vectors, retrovirus vectors, and the like.

As used herein, "3' overhanging portion" means a single stranded region at the 3' terminus of one strand of a double-stranded nucleic acid.

As used herein, the term "end" refers to both strands collectively at an end of a nucleic acid, and the term "terminus" refers to one strand individually at an end of a nucleic acid.

As used herein, a "limited digestion" means the exonucleolytic cleavage of some, but not all, residues of a nucleic acid, from a terminus of a strand. For example, a limited digestion using the enzyme lambda exonuclease digests the 5' termini of a nucleic acid strand.

As used herein, "single stranded gaps" means a single stranded region of a nucleic acid wherein the surrounding regions are double stranded.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a constitutive, inducible, or tissue specific manner.

As used herein, an "open reading frame" is a nucleotide sequence which, when analyzed as consecutive triplet codons, encodes a continuous amino acid sequence, i.e., an amino acid sequence not interrupted by stop codons.

Two open reading frames or two portions of a single open reading frame are "in frame" (or "in phase") if, in a single polynucleotide comprising the two open reading frames, consecutive triplet codons of the two open reading frames or portions encode a single continuous amino acid sequence.

Description

The recombination method of the invention is now described. The invention includes a method for recombining nucleic acids and then, optionally, cloning the recombined nucleic acids in a microorganism. The nucleic acids may be obtained from sources such as human, animal, plant, yeast, bacterial, or viral cDNAs, extrachromosomal DNAs, or cDNAs derived from cellular RNA, genomic DNAs, plasmids, and bacteriophage DNA (lambda and P1).

The method of the invention recombines an 'insert' nucleic acid having an end and a 'recipient' nucleic acid having an end. The end of each of the insert and recipient nucleic acids comprises a portion having an identical or very nearly identical sequence. These identical sequences may, for example, fortuitously have identical ends, or be amplified using a pair of PCR primers having an identical portion to yield amplified nucleic acids having identical ends. The identical regions on each end are situated where the insert nucleic acid and the recipient nucleic acid are to be joined, herein designated the "junctions of recombination."

The 3' overhanging portions are formed by performing a limited digestion of both the insert nucleic acid and the recipient nucleic acid. For example, the 5' termini may be digested using lambda exonuclease for about 15–20 seconds at 10° C. to remove about 10 to about 40 nucleotide residues at the ends of each of the two nucleic acids. The overhanging portions are complementary because the sequences of the double-stranded ends are identical.

The nucleic acids are hybridized by annealing the 3' overhanging portions of the insert nucleic acid and the recipient nucleic acid to yield a recombined nucleic acid having single stranded gaps. The single stranded gaps may be closed by extending the 3' terminus of a strand which borders the gap enzymatically or chemically to yield a double stranded recombined nucleic acid. This recombined nucleic acid can, optionally, be introduced into a microorganism for cloning.

The method of the invention recombines an insert nucleic acid and a recipient nucleic acid. The nucleic acids may be substantially any nucleic acids, and can be either DNA or RNA molecules, or a hybrid thereof. In a preferred embodiment, both nucleic acids are DNA. The nucleic acids may be either a linear molecule, such as a fragment, or a circularized molecule, such as a plasmid vector. If a circularized molecule is used, an end is created in the circularized molecule to allow insertion of the insert nucleic acid into the recipient nucleic acid. An end can be created in a circularized molecule using methods well known to the skilled artisan. Such methods include using PCR to create a linear molecule from a circularized molecule, using a non-specific endonuclease or UV light to create random strand breaks or by using a restriction enzyme.

The insert nucleic acid may be a linear molecule (e.g. a double stranded linear DNA molecule) and the recipient nucleic acid may be a circularized molecule (e.g. a double stranded plasmid). The method of the invention may be used to recombine, for example, nucleic acids which are not double stranded or which are double stranded and have gaps or single stranded regions.

The insert nucleic acid and recipient nucleic acid may be prepared by any nucleic acid preparation method available to the artisan skilled in the preparation of nucleic acids, including chemical synthesis and enzymatic synthesis using polymerase enzymes and PCR.

In one embodiment, at least one of the nucleic acids is prepared using PCR. In a preferred embodiment, both the insert and recipient nucleic acid are prepared by PCR. The invention also includes nucleic acids that are prepared by two different methods, such as partial chemical synthesis followed by PCR.

The insert and recipient nucleic acid may have substantially any length. However, when one nucleic acid is prepared by PCR, the maximum size of a fragment that can be cloned by this method is limited by the PCR procedure, which can produce up to about a 20 kilobase fragment. Plasmid vectors can incorporate insert nucleic acids of about 10–20 kilobases, and bacteriophage vectors, such as the P1 vector, can incorporate inserts of more than 100 kilobases. Limited digestion of the shortest fragment should generate a single stranded region having a length sufficient for hybridization yet preserve enough double stranded region to keep the duplex stable. For example, a PCR fragment having a length as small as 89 nucleotide residues was cloned successfully by this method.

The insert and recipient nucleic acids may be independently obtained from sources such as human, animal, plant, yeast, bacterial, or viral cDNAs, extrachromosomal DNAs, or cDNAs derived from cellular RNA, genomic DNAs, plasmids, and bacteriophage DNA (lambda and P1). In a preferred embodiment, the insert nucleic acid comprises a promoter/regulatory sequence and an open reading frame. This nucleic acid may be introduced into a microorganism for cloning following recombination. Of course, a nucleic acid that does not encode a polypeptide can also be recombined using the method of the invention.

Figure 1A:
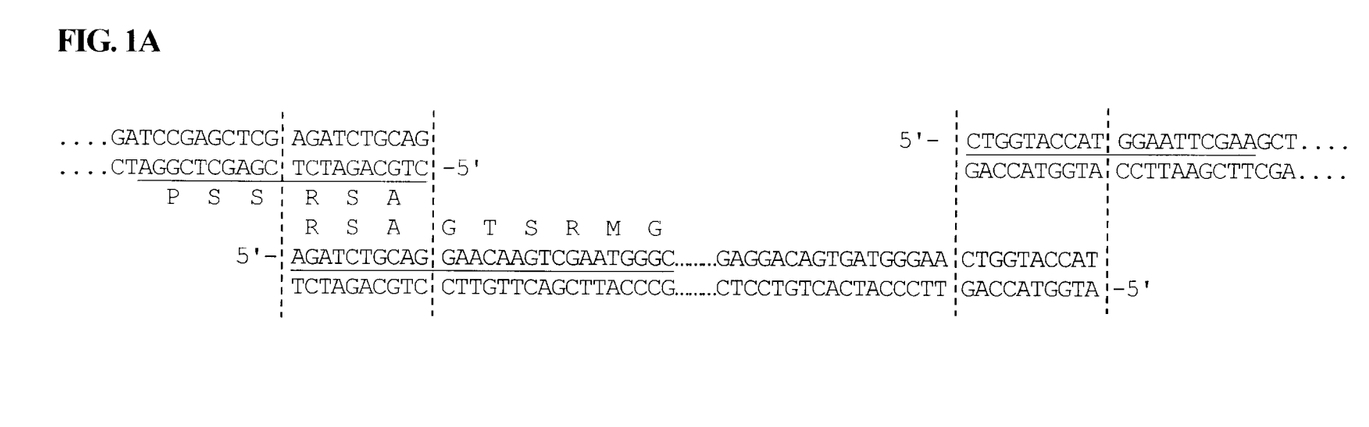
FIG. 1A lists the DNA sequence (SEQ ID NO: 1) and the DNA sequence (SEQ ID NO: 2) of the vector and the DNA sequence (SEQ ID NO: 3) and the DNA sequence (SEQ ID NO: 4) of the insert on the left end.
Figure 1B:
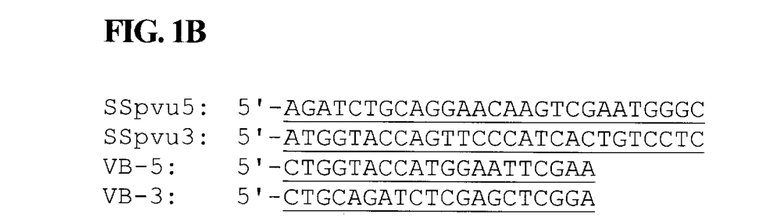
FIG. 1B lists the DNA sequences of the PCR primers used to produce the insert nucleic acid (SSpvu5: SEQ ID NO: 3 and SSpvu3: SEQ ID NO: 6) and the recipient nucleic acid (VB-5: SEQ ID NO: 5 and VB-3: SEQ ID NO: 1). The sequences include complementary regions as described herein, indicated by vertical dashed lines.
Figure 2A:
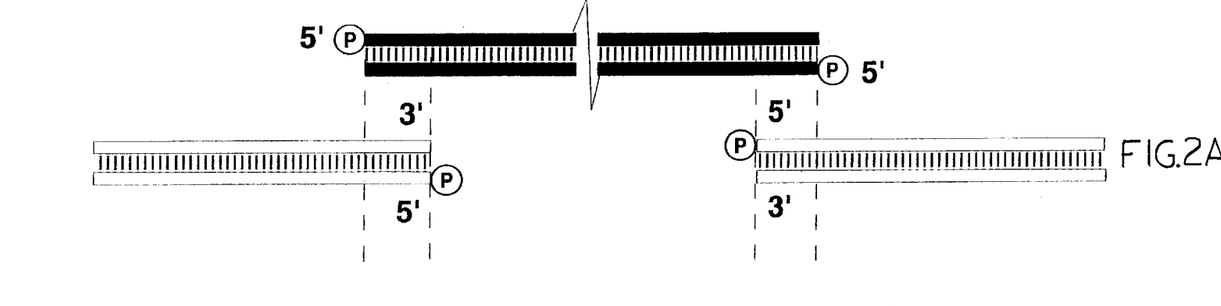
FIG. 2A depicts blunt ended DNA fragments having complementary regions indicated by dashed lines. The zig-zag line in the vector indicates an intervening sequence. The open bars represent recipient nucleic acid. The solid bars represent insert nucleic acid. The 5' termini of the nucleic acids are phosphorylated.

In the present invention, the 3' overhanging portions of the insert and recipient nucleic acids are complementary, such that when contacted, the 3' overhanging portions of each nucleic acid are capable of annealing. The 3' overhanging portions may be naturally occurring or artificial. These portions may be Generated using an available restriction site, if desired. In a preferred embodiment, PCR primers comprising identical portions are used to prepare the insert and recipient nucleic acids. This embodiment is illustrated in FIGS. 1 and 2. FIG. 1 depicts the PCR primers and the resulting insert and recipient nucleic acids comprising identical regions. The complementary strands of the identical regions enable one strand from each of the nucleic acids to be annealed.

The length of the complementary regions is important. These complementary regions may, for example, each have a length from about 3 to about 10 nucleotide residues. In one embodiment, the length of the complementary regions is 5 nucleotide bases. The length of the complementary regions should be less than about half of the length of the shorter nucleic acid.

Annealing of the complementary regions of the insert and recipient nucleic acids can only occur if the 3' overhanging portions are single-stranded. If an insert or recipient nucleic acid is double stranded, the 5' terminus of at least one end of the nucleic acid is digested to create a single-stranded 3' overhanging portion.

Limited digestion of a 5' terminus may be accomplished enzymatically. In one embodiment, an exonuclease enzyme is used to digest the nucleic acid. For example, a 5'→3' exonuclease such as lambda exonuclease may be used to digest the 5' termini of both the insert and recipient nucleic acid. Limited 5'→3' exonuclease digestion of the 5' terminus of one end of the insert nucleic acid forms a 5' digested insert terminus and a 3' overhanging insert portion on that end. Limited digestion of the other end of the insert nucleic acid forms a 5' digested insert terminus and a 3' overhanging insert portion on that other end. Similarly, limited 5'→3' exonuclease digestion of the 5' terminus of an end of the recipient nucleic acid forms a 5' digested recipient terminus and a 3' overhanging recipient portion on that end. Limited digestion of the 5' terminus of the other end of the recipient nucleic acid forms a 5' digested recipient terminus and a 3' overhanging recipient portion on that other end. The insert and recipient nucleic acids depicted in FIG. 2B have undergone limited digestion of their 5' termini.

Digestion of the 5' termini of the insert and recipient nucleic acids may be performed in separate reaction mixtures or in a single reaction mixture. Preferably, limited digestion of the insert and recipient nucleic acids is carried out in a single reaction mixture.

Preferably, digestion of 5' termini of the recipient nucleic acid and the insert nucleic acid yields 3' overhanging portions which have approximately the same length. The length of the 3' overhanging portions should be longer than the complementary region length to prevent destabilization of the nucleic acid duplex. For example, the length of the 3' overhanging portions may be equal to or greater than the complementary region length. The 3' overhanging portions may, for example, have a length from about 20 to about 30 nucleotide residues. Control can be exerted over the length of the overhanging portions by rapidly terminating the digestion reaction, either by lowering the temperature of the reaction mixture to below about 4° C., for example to 0° C., or by adjusting the pH to a suboptimal value (Little, 1981, Lambda Exonuclease: Gene Amplification and Analysis. Eds. J. G. Chirikjian and T. S. Papas, Elsevier, pp. 135–145). For example, the pH optimum for lambda exonuclease is pH 9.4. By lowering the pH to 7.0, a reaction rate of only 16% of the optimum rate is obtained. If the reaction is terminated by using a suboptimal pH, the pH should not be lowered to below pH 3 to avoid depurination of DNA. Either suboptimal pH or low temperature may be used to terminate the reaction. Digestion may also be terminated by both lowering the temperature and adjusting the pH. For example, lambda exonuclease digestion can be terminated very rapidly by adding an ice-cold (i.e., 0° C.) 0.3 molar solution of sodium acetate at pH 5.3. This solution is effective at both stopping the reaction and precipitating digested DNA using ethanol or other solvents. For example, the DNA can be precipitated by adding about 2.5 volumes of 100% ethanol to the 0.3 molar solution of sodium acetate at pH 5.3. Other solvents which can be used in the termination of the digestion reaction and precipitation of DNA include ethanol, isopropanol, 0.2 molar potassium acetate, 1 molar sodium chloride, about 1 molar ammonium acetate, and combinations thereof.

The exonuclease used in the method of the invention may, for example, be lambda exonuclease. Lambda exonuclease has a substrate preference for 5' termini which are phosphorylated, and for blunt end DNA (Little, 1981, Lambda Exonuclease: Gene Amplification and Analysis. Eds. J. G. Chirikjian and T. S. Papas, Elsevier, pp. 135–145). The lambda exonuclease reaction can still proceed without blunt end and/or phosphorylated 5' end, but the reaction rate is about 1/100th of the rate obtained using a blunt end DNA with 5' phosphate. Therefore, the insert and recipient nucleic acids preferably have phosphorylated 5' ends. For example, 5' phosphorylated nucleic acids may be generated using 5' phosphorylated PCR primers using thermostable DNA polymerases to generate blunt-ended nucleic acids. Examples of such DNA polymerases are Pfu thermophilic DNA polymerase (Stratagene, La Jolla, Calif.) and Vent thermophilic DNA polymerase (New England Biolabs, Beverly, Mass.). Non-phosphorylated PCR primers can also be used, and the PCR product can be phosphorylated using a kinase enzyme.

The duration of lambda exonuclease digestion is preferably very short and is temperature dependent. For example, at about 10° C., the reaction time is preferably from about 10 to about 20 seconds, and at about 7° C., the reaction time is preferably from about 20 to about 30 seconds. Shorter durations may be used, however, durations of less than about 5 seconds may be too brief to be experimentally practical.

In a preferred embodiment, the complementary 3' overhanging insert portion and 3' overhanging recipient portion are hybridized by maintaining the hybridization reaction at from about 40° C. to about 65° C. for about 1 hour or longer and then cooling to below about 35° C. For example, the reaction can be maintained at 55° C. for 1 hour and then cooled to room temperature. The reaction can also be cooled below room temperature using refrigeration.

Figure 2B:
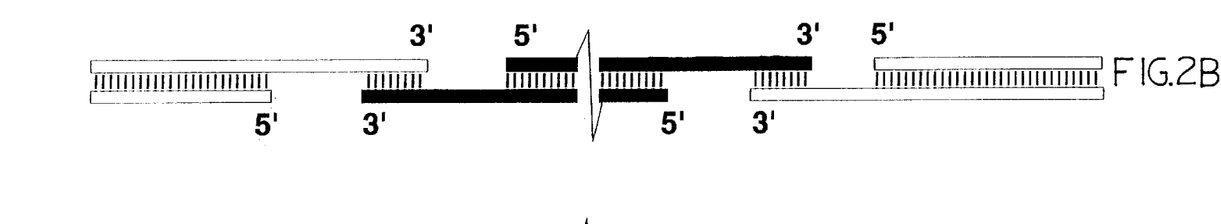
FIG. 2B depicts the nucleic acids after a limited digestion by lambda exonuclease. Short 3' overhanging portions are produced on both 3' termini of the insert nucleic acid and the recipient nucleic acid.
Figures 2C, 2D:
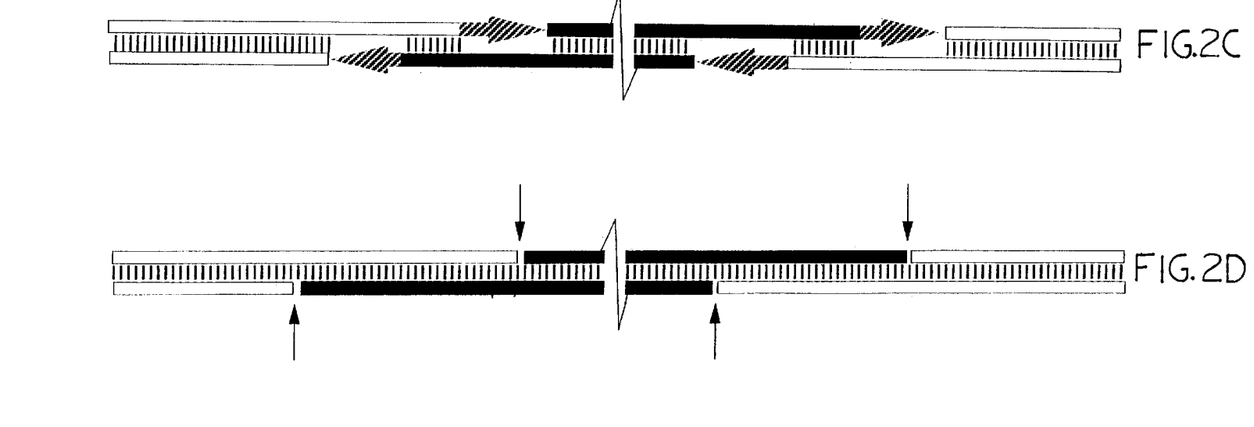
FIG. 2C depicts the closing of single stranded gaps on the recombined nucleic acid using the modified (3'→5' exo-) Klenow fragment of *E. coli* DNA polymerase I (New England Biolabs, Beverly, Mass.). The direction of DNA synthesis is indicated by striped arrows.
FIG. 2D depicts the junctions of recombination prior to introducing the recombined nucleic acid into *E. coli* for cloning. Nicks are indicated by vertical arrows.

Under these conditions, the 3' overhanging portions of the insert nucleic acid and the recipient nucleic acid anneal, and the nucleic acids are thereby recombined, as depicted in FIG. 2B. The recombined nucleic acid has single stranded nicks or gaps, as depicted in FIG. 2B because the overhanging portions may be longer than the complementary regions. If subsequent cloning of the recombined nucleic acid is desired, single stranded gaps should be closed. The gaps can be closed by an enzymatic method. Such enzymatic methods are well-known to the skilled artisan. For example, the gaps may be closed using a gap closing enzyme such as a DNA polymerase enzyme (e.g. T4 DNA polymerase) or a DNA repair enzyme (e.g. the modified {3'→5' exo-} Klenow fragment of E. coli DNA polymerase I). These gap closing enzymes elongate the hybridized 3' overhanging portions and stabilize the junction without strand displacement, as depicted in FIG. 2C.

The gap closing enzyme is preferably a DNA polymerase or DNA repair enzyme lacking 3'→5' exonuclease activity. The modified (3'→5' exo-) Klenow fragment of E. coli DNA polymerase I (Derbyshire et al., 1988, Science 240:199–201) is one such enzyme. Klenow (3'→5' exo-) is preferred because it consistently produced a greater number of recombinants than T4 DNA polymerase in experiments described herein in the Example. Presumably, Klenow does not digest the 3' overhanging portions, and thus does not adversely effect the recombination. T4 DNA polymerase has 3'→5' exonuclease activity.

A 3'→5' exonuclease may also be used in the method of the invention to digest insert and recipient nucleic acids. Digestion at the 3' termini forms 5' overhanging portions which are complementary and may be annealed. Hybrids formed by the 5' overhanging portions are not stabilized by the single stranded gap closing process. Therefore, in order to achieve results in subsequent cloning similar to those achievable using nucleic acid recombined using a 5'→3' exonuclease, longer complementary regions should be used. An example of a 3'→5' exonuclease is Exonuclease III.

In one embodiment of the invention, the recombined double stranded nucleic acid is cloned by introducing it into a microorganism after closing any gaps in the nucleic acid. A preferred microorganism for cloning is E. coli.

The invention also includes a kit comprising an enzyme for digesting a 5' terminus of a double stranded nucleic acid, another enzyme for closing gaps in a double stranded nucleic acid, and instructional material for use in carrying out a nucleic acid recombination method described herein. The kit may further comprise one or more of controls, buffers, tubes, and nucleic acids. For example, the kit may include a control vector and insert. The control vector and insert may be used along with other experimental materials and instructional material in the kit to ensure proper functioning of all components.

The invention also includes recombined nucleic acids made using a method of the invention.

The invention is now described with reference to the following Example. This Example is provided for the purpose of illustration only, and the invention should in no way be construed as being limited to this Example, but rather should be construed to encompass any and all variations which become evident as a result of the teaching provided herein.

EXAMPLE

Recombining Plasmid and Insert DNA to Yield in Frame Coding Sequence for Basonuclin Followed by Cloning in *E. coli*

In this Example, the method of the invention was used to join a DNA fragment encoding the serine stripe of basonuclin (Tseng et al., 1992, Proc. Natl. Acad. Sci. USA 89:10311–10315) and the C-terminus of the histidine tag of the pRSET-B plasmid (Invitrogen, Carlsbad, Calif.) in frame. In this Example, the DNA fragment encoding the serine stripe of basonuclin represents the insert nucleic acid, and the pRSET-B plasmid represents the recipient nucleic acid. None of the restriction sites of the multiple cloning site of the pRSET-B plasmid flank the serine stripe sequence. Thus, recombining these nucleic acids using traditional recombination methods would be very difficult or impossible.

The materials and methods used in the experiments presented in this Example are now described.

Preparation of Insert Nucleic Acid and Recipient Nucleic Acid

The 2.9 kilobase pRSET-B sequence was prepared by PCR using primers VB5 and VB3, which are shown in FIG. 1B. The 210 nucleotide residue insert fragment was prepared by PCR using primers SSpvu5 and SSpvu3, which are also depicted in FIG. 1B. Primer SSpvu5 contained a 10 nucleotide residue region which was complementary with a region of primer VB3, and primer SSpvu3 contained a 10 nucleotide residue region which was complementary with a region of primer VB5, as depicted in FIG. 1B. All primers were 5' phosphorylated, and the PCR reactions used the Pfu thermophile polymerase obtained from Stratagene (La Jolla, Calif.). The PCR prepared nucleic acids were then purified using an 0.4 milliliter packed bed volume DEAE-Sephacel column (Amersham-Pharmacia Biotech Inc., Piscataway, N.J.). DNA was loaded onto the column in a solution of 0.3 molar NaCl in TE buffer (10 millimolar Tris-HCl, pH 8.0 and 1 millimolar EDTA) and eluted in 0.4 milliliters of 1 molar NaCl in TE buffer. All residual eluant in the column was displaced with a syringe and collected. DNA was precipitated using 1 milliliter of ethanol without using carrier tRNA.

Limited Digestion of the Nucleic Acids

The 5' termini of insert and recipient nucleic acids were digested in a single reaction mixture comprising an exonuclease to yield single stranded 3' overhanging portions having lengths of about 20–30 nucleotide residues. The digestion reaction was initiated by combining 200–300 nanograms each of DEAE-purified recipient and insert nucleic acid in 20 microliters of a solution containing 67 millimolar glycine-NaOH at pH 9.4, 2.5 millimolar $MgCl_2$, and 32 units of lambda exonuclease (Pharmacia LKB Biotechnology Inc., Piscataway, N.J.) at 10° C. for 20 seconds in a thermocontroller. The digestion reaction was terminated by adding 0.2 milliliters of 0.3 molar sodium acetate at pH 5.3 and 0° C. The mixture was immediately extracted by adding an equal volume of phenol:chloroform:amyl alcohol (25:24:1) vortexing the mixture, and transferring the aqueous phase to a fresh tube. DNA in the aqueous phase was precipitated using ethanol. Following this treatment, each of the recipient and insert DNA had 3' single stranded overhanging portions having lengths of approximately 15–20 nucleotide residues. The plasmid and insert DNA were resuspended in 5 microliters of a solution comprising 100 millimolar NaCl, 20 millimolar Tris-HCl, pH 7.9, 10 millimolar $MgCl_2$ and 1 millimolar dithiothreitol ("2×T4 DNA polymerase buffer").

The time course of lambda exonuclease digestion at various reaction temperatures was assessed as follows. A 2.5 microgram sample of Pvu II (New England Biolabs, Beverly, Mass.) digested pRSET-B plasmid was dissolved in 14 microliters of 67 millimolar glycine-NaOH at pH 9.4, and 2.5 millimolar $MgCl_2$ ("lambda exonuclease buffer"). The mixture was cooled to 22° C., 10° C. or 0° C. in a thermal controller, and 38 units of lambda exonuclease in 6 microliters of a solution of 10 millimolar Tris-HCl, 10 millimolar beta-mercaptoethanol, 500 micrograms per milliliter of bovine serum albumin and 50% (v/v) glycerol having a pH of 7.6 were quickly added.

Figure 3A:
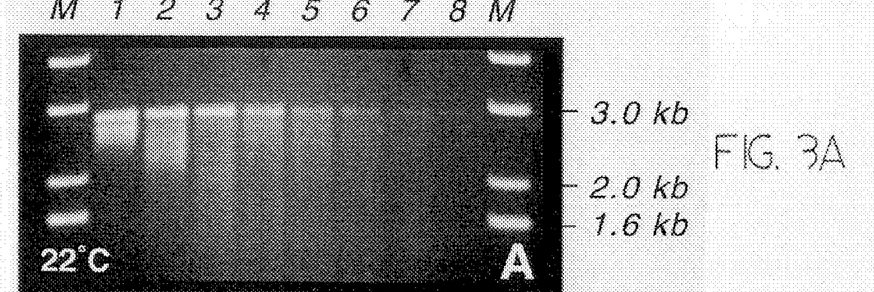
Figure 3B:
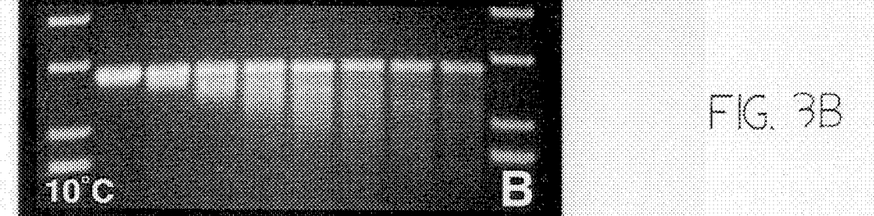
Figure 3C:
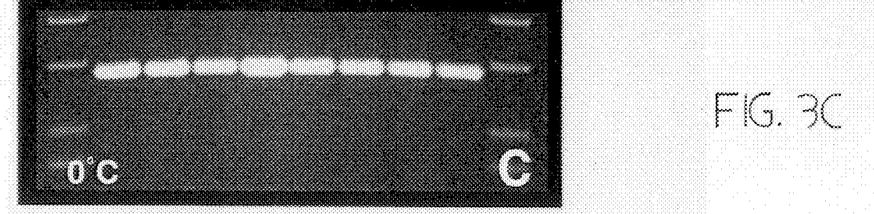

At time intervals of 0.5, 1, 2, 3, 4, 5, 6, and 7 minutes after exonuclease addition, a 2 microliter sample was removed and mixed with 8 microliters of an ice cold solution comprising 0.3 molar potassium acetate, pH 4.6, 2.5 molar NaCl, 10 millimolar $ZnSO_4$, 50% (v/v) glycerol, and 2.5 units of S1 nuclease (Promega Corp., Madison, Wis.) ("S1 buffer") to halt the exonuclease digestion. After all data were gathered, the tubes containing S1 buffer were removed from the ice and maintained at room temperature to commence S1 nuclease digestion. S1 nuclease digestion was continued for 30 minutes, and was terminated by adding 1 microliter of a solution comprising 0.3 molar Tris base and 0.05 molar EDTA having a pH of 9 or higher. The contents of each tube were electrophoresed using 1% agarose gels. Images of these gels are shown in FIGS. 3A, 3B, and 3C. The results shown in FIGS. 3A and 3B indicate that for lamba exonuclease, the synchrony of digestion breaks down quickly.

The results of experiments using low temperature to terminate the digestion reaction are shown in FIG. 3. Between 50–100 bases were removed from each end in the first minute when the digestion was performed at 10° C. When the DNA substrate was in excess, the length of overhanging portion produced, which is directly related to the number of recombinants obtained, was proportional to the amount of exonuclease used. The data from this experiment indicate that to maintain synchrony of digestion for lambda nuclease, the digestion temperature should range from about 5° C. to about 15° C. and the digestion time should range from about 5 to about 60 seconds. Preferably, the digestion is at 10° C. for 15–20 seconds, and results in the removal of 20–30 nucleotide residues at each 5' terminus.

The effect of varying the length of the complementary regions on the number of recombinants obtained is indicated by the data listed in Table 1. Using the methods described herein, nucleic acids having complementary regions of lengths from 3 to 10 nucleotide residues were tested. The complementary region in the PCR primer SSpvu5 was 10, 7, 5, or 3 nucleotide residues, and the length of the complementary region in the PCR primer SSpvu3 was constant at 10 residues. The data from the experiment are depicted in Table 1, which indicates that recombinants are possible with a complementary region length as small as 3 nucleotide residues. The preferred length is from 5 to 10 nucleotide residues.

Annealings of Nucleic Acids

The insert and recipient nucleic acids were hybridized by submerging the tube containing the resuspended DNA mixture in a one liter container of water at 55° C. to anneal the 3' overhanging portions on the insert and recipient nucleic acids. The reaction mixture was then allowed to cool at room temperature to 30° C.

Closing Single Stranded Gaps in the Recombined DNA

Single stranded gaps which remained after hybridization of the overhanging portions on the recipient and insert nucleic acids were closed using the modified (3'→5' exo-) Klenow fragment of E. coli DNA polymerase I (New England Biolabs, Beverly, Mass.). 5 microliters of a solution containing 5 Units of Klenow (3'→5' exo-) and 250 micromolar of each deoxynucleoside triphosphate (i.e. A, T, G, and C) was added to the hybridized nucleic acid. The reaction mixture was incubated at room temperature for 30 minutes to close single stranded gaps in the recombined nucleic acid.

Cloning the Recombined DNA in E. coli

The recombined nucleic acid was diluted with 10 microliters of TE buffer to a final volume of about 20 microliters. About 5 microliters of this mixture was used to transform E. coli strain DH5α (GIBCO/BRL, Grand Island, N.Y.). About 100–200 recombinants and a 1:20 background (vector alone) to recombinant ratio were usually obtained. Four colonies from the recombinant group were selected and sequenced and the remaining colonies were pooled. A Bgl II (New England Biolabs, Beverly, Mass.) digestion of DNA obtained from the pooled colonies indicated that a majority of the clones contained a 200 base pair insert. The results obtained from the sequencing of the four randomly selected clones confirmed that all eight junctions during recombination were formed as predicted

TABLE 1

The Number of Recombinants Obtained as a Function of Complementary Region Length

| Length in Number of Nucleotide Residues of the Complementary Region | Numbers of Recombinants (average of two experiments) |
|---|---|
| 10 | 111 |
| 7 | 109 |
| 5 | 57 |
| 3 | 16 |
| Control-1 (vector only) | 6 |
| Control-2 (vector with an incompatible insert) | 5 |

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of recombining an insert nucleic acid and a vector nucleic acid, said method comprising
   a) digesting the 5' terminus of an end of said insert nucleic acid to yield a 3' overhanging insert portion and a 5' digested insert terminus;
   b) digesting the 5' terminus of an end of said vector nucleic acid to yield a 3' overhanging vector portion and a 5' digested vector terminus, wherein said 3' overhanging vector portion and said 3' overhanging insert portion are complementary; and
   c) thereafter annealing said 3' overhanging vector portion and said 3' overhanging insert portion to yield a double stranded complementary region, whereby said insert nucleic acid and said vector nucleic acid form a recombined nucleic acid, wherein both said insert nucleic acid and said vector nucleic acid are prepared by PCR and further wherein neither said insert nucleic acid nor said vector nucleic acid is prepared using a restriction endonuclease.

2. The method of claim 1, further comprising
   d) closing single stranded gaps in said recombined nucleic acid.

3. The method of claim 2, wherein said single stranded gaps are closed using an enzyme selected from the group consisting of a DNA polymerase and a DNA repair enzyme.

4. The method of claim 3, wherein said DNA polymerase is T4 DNA polymerase.

5. The method of claim 3, wherein said enzyme lacks 3'→5' exonuclease activity.

6. The method of claim 5, wherein said 3' overhanging portions have a uniform length of from about 20 to about 30 nucleotide bases.

7. The method of claim 3, wherein said DNA repair enzyme is the modified (3'→5' exo-) Klenow fragment of E. coli DNA polymerase I.

8. The method of claim 2, further comprising
   e) introducing said recombined nucleic acid into a microorganism after closing said single stranded gaps.

9. The method of claim 1, wherein said complementary region has a length from about 3 to about 10 nucleotide residues.

10. The method of claim 1, wherein said 5' termini are digested using an 5'→3' exonuclease.

11. The method of claim 10, wherein said 5'→3' exonuclease is lambda exonuclease.

12. The method of claim 1, wherein said insert nucleic acid and said recipient nucleic acid are phosphorylated at their 5' termini.

13. The method of claim 12, wherein said PCR reaction is carried out using a thermophile polymerase and wherein said nucleic acid has blunt ends.

14. The method of claim 1, wherein said recombined nucleic acid comprises a promoter/regulatory sequence and an in-phase open reading frame.

15. The method of claim 1, wherein said insert nucleic acid is selected from the group consisting of a nucleic acid obtained from a human and a nucleic acid encoding a therapeutic agent.

16. A method of recombining an insert nucleic acid and a vector nucleic acid, said method comprising
   a) digesting the 3' terminus of an end of said insert nucleic acid to yield a 5' overhanging insert portion and a 3' digested insert terminus;
   b) digesting the 3' terminus of an end of said vector nucleic acid to yield a 5' overhanging vector portion and a 3' digested vector terminus, wherein said 5' overhanging vector portion and said 5' overhanging insert portion are complementary; and
   c) thereafter annealing said 5' overhanging vector portion and said 5' overhanging insert portion, whereby said insert nucleic acid and said vector nucleic acid form a recombined nucleic acid, wherein both said insert nucleic acid and said vector nucleic acid are prepared by PCR and further wherein neither said insert nucleic acid nor said vector nucleic acid is prepared using a restriction endonuclease.

17. The method of claim 16, wherein said 3' termini are digested using Exonuclease III.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: plasmid
      vector pRSET-B left end

<400> SEQUENCE: 1
ctgcagatct cgagctcgga                                              20

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: plasmid
      vector pRSET-B left end

<400> SEQUENCE: 2

Pro Ser Ser Arg Ser Ala
 1               5

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Basonuclin
      serine stripe sequence, left end -continued

```
<400> SEQUENCE: 3
agatctgcag gaacaagtcg aatgggc                                              27

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Basonuclin
      serine stripe sequence, left end

<400> SEQUENCE: 4

Arg Ser Ala Gly Thr Ser Arg Met Gly
  1               5

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Plasmid
      vector pRSET-B, right end

<400> SEQUENCE: 5
ctggtaccat ggaattcgaa g                                                    21

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Basonuclin
      serine stripe sequence, right end

<400> SEQUENCE: 6
atggtaccag ttcccatcac tgtcctc                                              27
```